United States Patent [19]

Azzam

[11] 4,306,809

[45] Dec. 22, 1981

[54] POLARIMETER

[75] Inventor: Rasheed M. A. Azzam, Omaha, Nebr.

[73] Assignee: The Board of Regents of the University of Nebraska, Lincoln, Nebr.

[21] Appl. No.: 23,689

[22] Filed: Mar. 26, 1979

[51] Int. Cl.$^3$ .................. G01N 21/21; G01U 4/04; G02F 1/01; G02F 1/09

[52] U.S. Cl. ........................ 356/368; 350/377; 350/393; 350/403; 350/407; 356/365; 356/369

[58] Field of Search ................ 356/364–369; 250/225; 350/150–151, 157, 376, 393, 403, 407

[56] References Cited

U.S. PATENT DOCUMENTS

| | | | |
|---|---|---|---|
| 2,780,958 | 2/1957 | Wiley | 350/150 |
| 3,558,214 | 1/1971 | De Lang et al. | 350/151 |
| 3,558,215 | 1/1971 | De Lang et al. | 350/151 |
| 3,612,688 | 10/1971 | Liskowitz | 356/364 |
| 3,985,447 | 10/1976 | Aspnes | 356/370 |

OTHER PUBLICATIONS

Hauge et al., "A Rotating-Compensator Fourier Ellipsometer" Optics Communications, 8–1975, pp. 431–437.
Aspnes et al., "Rotating-Compensator/Analyzer Fixed-Analyzer Ellipsometer: Analysis & Comparison to Other Automatic Ellipsometers", Jr. Optical Soc. America, 9-1976, pp. 949–954.
Azzam, R. M. A., "Photopolarimetric Measurement of the Mueller Matrix by Fourier Analysis of a Single Detected Signal", Optics Letters, 6-1978, pp. 148–150.
Thompson et al., "Polarization-Dependent Ligh-Scattering Measurements Using an Electro-Optical Modulator-Based Instrument" Optical Polarimetry, vol. 112 1977, pp. 152–157.
Azzam, R. M. A. "Simulation of Mechanical Rotation by Optical Rotation: Application to the Design of a NE Photopolarimeter", J. Opt. Soc. A. vol. 68, 4-1978, pp. 518–521.
Azzam, R. M. A. "Photopolarimeter Using Two Modulated Optical Rotators", Optics Letters, 11-1977, pp. 181–183.
Azzam, R. M. A., "Fourier Photoellipsometers & Photopolarimeters Based on Modulated Optical Rotation", Optical Polarimetry vol. 112, 1977 pp. 54–57.

Primary Examiner—William H. Punter
Attorney, Agent, or Firm—Vincent L. Carney

[57] ABSTRACT

To measure characteristics such as density and particle-size distributions of a medium that interacts with light, a polarimeter simultaneously develops all 16 elements of the Mueller matrix by modulating polarized monochromatic light with a quarter-wave retarder operating at a predetermined frequency before transmitting it to the medium and then modulating the light leaving the medium with another quarter-wave retarder which operates at a frequency five times that of the predetermined frequency of modulation of the light transmitted to the medium. The light is electrically detected and provides a signal which may, by Fourier analysis, be broken into 25 terms. The coefficients of those 25 terms, by relatively easy calculations, provide the 16 elements of the Mueller matrix. An electrical element is provided for optically simulating the rotation of a quarter-wave retarder.

29 Claims, 5 Drawing Figures

POLARIMETER

This invention relates to polarimeters.

In one type of polarimeter, polarized light is transmitted to a medium and modulated either before or after it reaches the medium or both before it reaches the medium and after. The light which is reflected from the medium or passed through it is measured and used to construct a Mueller matrix which identifies certain characteristics of the medium.

In one prior art type of polarimeter of this class, four wave retarders are vibrated to modulate the light both entering the medium and leaving the medium.

This prior art polarimeter has the disadvantage of being complicated. It is complicated because of the multiple modulators that are required and because of the difficulty of analyzing the electrical signal generated by the detector to form a Mueller matrix which identifies characteristics of the medium. The polarimeters that modulate the light either before or after interacting with the medium are unable to provide sufficient information for a Mueller matrix without extensive measurements and calculations.

Accordingly, it is an object of the invention to provide a novel polarimeter.

It is a further object of the invention to provide a novel method of measuring certain characteristics of a medium by its interaction with light.

It is a still further object of the invention to provide a novel ellipsometer.

It is a still further object of the invention to provide a simple universal polarimeter.

It is a still further object of the invention to provide a polarimeter in which a single signal can provide a simultaneous identification of the 16 elements of a Mueller matrix.

It is a still further object of the invention to provide a polarimeter in which an electrical signal is generated by light interacting with a medium and Fourier analysis provided on that light to provide 25 coefficients which are sufficient to identify the 16 elements of a Mueller matrix.

It is a still further object of the invention to provide a novel mechanism for optically rotating an optical element.

In accordance with the above and further objects of the invention, a polarimeter includes a source of monochromatic light, first and second polarizers, and first and second quarter-wave retarders. The first polarizer is fixed in position and receives the light from the source of light. The first quarter-wave retarder modulates the light passing through the first polarizer at a predetermined frequency and applies it to a medium, characteristics of which are to be measured. The second quarter-wave retarder modulates the light at a frequency of five times or else one-fifth of the first quarter-wave retarder after the light has interacted with the medium. The second polarizer returns the polarized light to the original (or another fixed) axis and transmits it to a detector.

A Fourier signal analyzer analyzes the electrical signal generated by the detector in response to the light and generates coefficients which may be used to calculate the elements of the Mueller matrix with relatively simple arithmetic operations such as adding and subtracting and multiplying or dividing by constants. This may be done with a small computer.

To rotate an optical element, which may be a quarter-wave retarder in an embodiment of the invention, light is rotated in one direction through an angle on one side of the retarder and then through the same angle on the other side of the retarder as a substitute for rotating the retarder. This mechanism may be used to rotate optically any optical element through which light is transmitted, and, advantageously, the light may be rotated by Faraday cells which receive equal and opposite potentials from a single source.

As can be understood from the above description, the polarimeter of this invention has several advantages such as: (1) it is relatively simple and requires only two moving parts or electrical units that simulate the two moving parts; (2) it generates all 16 elements of the Mueller matrix and thus may be used to define the elastic interaction of the medium with light; (3) it generates redundant information which may be used to check on the internally generated noise of the circuit; and (4) it is fast and generates the Mueller matrix in an on-line, simultaneous manner.

The above noted and other features of the invention will be better understood from the following detailed description when considered in connection with the accompanying drawings in which.

Figure 1:
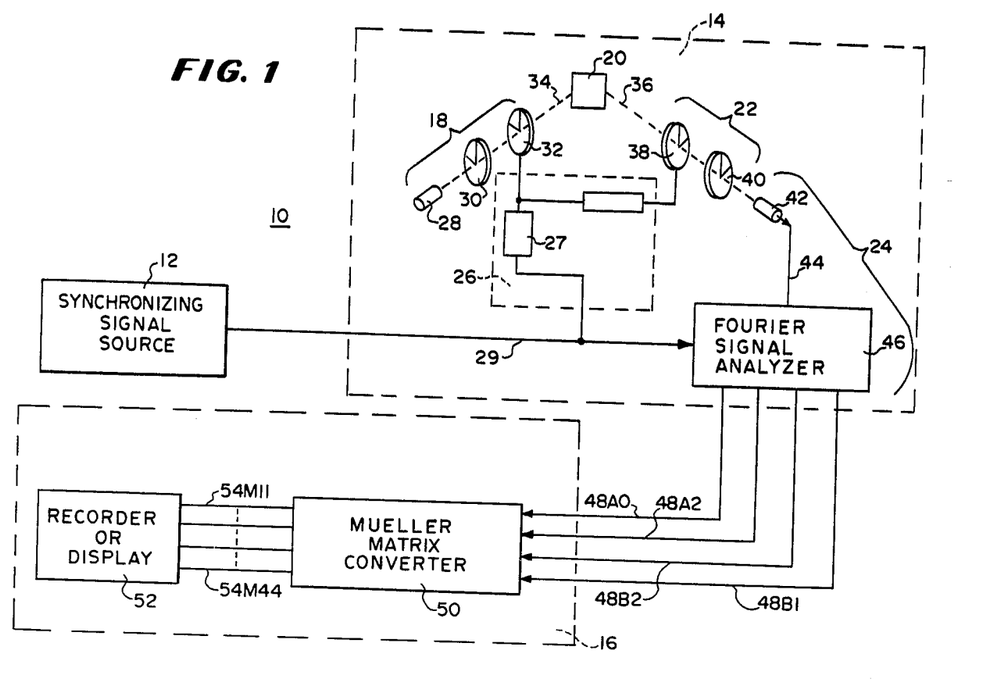
FIG. 1 is a simplified schematic diagram of a polarimeter in accordance with an embodiment of the invention.

In FIG. 1, there is shown a polarimeter 10 having a synchronizing signal source 12, an optical-electrical analyzer 14, and readout apparatus 16. The optical-electrical analyzer 14 develops an electrical signal which represents the characteristics of a medium being analyzed through the use of optical analysis and provides that signal to the readout system 16 which records values indicating those characteristics. The synchronizing signal source 12 provides synchronizing signals to the optical-electrical analyzer 14.

To optically analyze a medium, the optical-electrical analyzer 14 includes a source of modulated light 18, a sample cell 20, an optical analyzing system 22, a Fourier analysis unit 24, and modulator controller 26. The source of modulated light 18 applies a modulated beam of light to the material sample being analyzed in the sample cell 20 and the analyzing optics 22 analyzes that light and applies it to the electrical Fourier analyzer 24 which converts the light to electrical signals and provides an electrical output representing a Fourier analysis of the optical signal. The modulator controller 26 controls the source of modulated light 18 and the optical analyzing system 22 in a manner to be described hereinafter.

With this equipment, the polarimeter 10 serves as a universal polarimeter which provides an on-line readout of the optical characteristics of the substance, thus enabling it to serve as an ellipsometer for characterization of surfaces and thin films as well as a polarimeter for measuring the elastic interaction of light with any substance through which it passes such as particle suspensions, fog, haze, and the like.

To modulate the beam of light being applied to the sample cell 20, the source of modulated light 18 includes a monochromatic light source 28, a fixed polarizing element 30, and the quarter-wave retarder 32 all adapted to provide a beam of light 34 to the sample cell 20. The source of monochromatic light 28 applies a beam of light first through the fixed polarizing element 30 and from the fixed polarizing element 30 to the quarter-wave retarder 32 and from there to the sample cell 20. The quarter-wave retarder 32 modulates the beam of light with a frequency f.

The source of monochromatic light 28 is preferably a laser which generates light which interacts with the substance being analyzed in the sample cell 20. The fixed polarizer is a linear polarizer which has a fixed axis which is known. It polarizes the light and applies it to the quarter-wave retarder 32 which may be for example a rotating mica disc. Such discs are known in the art and consist of substantially a 1.5 millimeter-thick mica disc attached at one end to the shaft of a small synchronous motor which rotates at a selected frequency.

To modulate the beam of light 34, the disc 32 rotates about an axis perpendicular to and passing through the center of its wide surfaces in the path of the beam of light 34. Other types of quarter-wave retarders are known in the art and are available.

The sample cell 20 has transparent windows and is capable of holding the sample or may include a clamp to hold a film-coated substrate. It is positioned to receive light from the beam 34 and permit the light to pass through it or be reflected from it into a beam 36.

To analyze the light beam 36 which carries information about the substance being studied in the sample cell 20, the optical analyzing system 22 includes a quarter-wave retarder 38 and a fixed polarizing element 40. The light beam 36 passes through the quarter-wave retarder 38 and then through the fixed polarizing element 40 into the optical-electrical analyzer 24. The quarter-wave retarder 38 is synchronized with the quarter-wave retarder 32 to operate at a multiple of the frequency of the quarter-wave retarder 32. For example, if the quarter-wave retarder 32 is operating at a frequency f the quarter-wave retarder 38 operates at a frequency of 5 f. If the quarter-wave retarders 32 and 38 are discs, then the disc 32 is rotated at a speed 1/5 of the speed of the disc 38.

The fixed polarizing elements 30 and 40 may have any arbitrarily selected known axes. The quarter-wave retarders 32 and 38 are rotated in synchronism by the synchronous motor 27 which is driven by the signal from the synchronizing signal source 12. The disc 32 is driven directly from the shaft and the disc 38 is driven through a gear system that maintains the five to one ratio of rotation between the discs 32 and 38.

The light beam 36 after being analyzed is passed to a photodetector 42 which converts it to an electrical signal that is applied through a conductor 44 to a Fourier analyzer 46. The electrical signal on conductor 44 from the detector 42 includes 25 Fourier components which the Fourier signal analyzer 46 reduces to 25 separate amplitudes in a signal for application to the readout apparatus 16. The signals from the Fourier signal analyzer 46 are applied to an analog-to-digital converter and converted from serial to parallel form for recording. The recorded amplitudes then indicate the characteristics of the material in the sample cell 20.

To synchronize the modulator controller 26 and the Fourier signal analyzer 46, the synchronizing signal source 12 is electrically connected to both the modulator controller 26 and the Fourier signal analyzer 46 through a conductor 29. The frequency of the signal may be 60 cycles or any other suitable frequency chosen to operate with the modulator controller 26 and the analyzer 46. For example, if the modulator controller 26 includes a synchronous motor designed to operate from a 60 cycle mains supply, then the synchronizing signal source 12 may be the 60 cycle AC mains supply.

The Fourier signal analyzer 46 is of a type which provides the coefficients for each of the different frequencies for the Fourier series into 25 different conductors four of which, 48A0, 48A2, 48B2 and 48B1, are shown in FIG. 1 as an example. Each of the different coefficients is a time varying DC signal on a different one of the conductors indicating one of the Fourier coefficients of the signal on conductor 44. The Fourier signal analyzer 46 develops 25 varying DC signals or a zero potential.

Each of the 25 possible signals represents a different term of the Fourier series that is developed by the polarized light interacting with the medium in sample cell 20 when the light is modulated before and after interacting with the medium by synchronized quarter-wave retarders in a five to one ratio of modulation. Only 16 signals are necessary to fully identify the 16 elements of the Mueller matrix and the remaining signals are redundant and may be used for error checking or correcting. The analyzer 46 provides an output for each revolution of retarder 32 and five revolutions of disc 38 under the control of the synchronizing signal source 12. Suitable Fourier analyzers are commercially available.

The display 16 includes a Mueller matrix converter 50 and a recorder or display 52. The Mueller matrix converter 50 receives the 16 signals, four of which are 48A0, 48A2, 48B2 and 48B1 being shown in FIG. 1 and converts them to the 16 elements of a Mueller matrix which characterize the interaction of light with a medium, and therefore identify the medium.

Determination of a Mueller matrix for a medium by the Fourier analysis of light received from the medium is a known method for obtaining information about the medium with which the light interacts. The Mueller matrix is a 4×4 matrix which relates the Stokes vectors of light before and after its interaction with the sample. It is determined by the shape, refractive index, mean size and spread in the size distribution of scattering particles in the medium.

To determine the elements of the Mueller matrix for the medium in sample cell 20, the Mueller matrix converter 50 performs operations on signals representing the coefficients of the Fourier series from the Fourier signal analyzer 46 to obtain the coefficients of the Mueller matrix and apply them to the recorder or display 52. To perform this function, the Mueller matrix converter 50 receives 16 inputs and calculates 16 elements of the Mueller matrix from the 16 inputs.

The values of the Fourier amplitudes are indicated symbolically in Table 1 which designates each of the values if the coefficients of the Fourier series by 48A or 48B and by a number from 0 through 12.

TABLE 1

| n | 0 | 1 | 2 | 3 | 4 |
|---|---|---|---|---|---|
| $48A_n$ | $m'_{11} + \frac{1}{2}m'_{12} + \frac{1}{2}m'_{21} + \frac{1}{4}m'_{22}$ | 0 | $\frac{1}{2}m'_{12} + \frac{1}{4}m'_{22}$ | $-\frac{1}{4}m'_{43}$ | $-\frac{1}{4}m'_{44}$ |
| $48B_n$ |  | $m'_{14} + \frac{1}{2}m'_{24}$ | $\frac{1}{2}m'_{13} + \frac{1}{4}m'_{23}$ | $-\frac{1}{4}m'_{42}$ | 0 |

| n | 5 | 6 | 7 | 8 | 9 |
|---|---|---|---|---|---|
| $48A_n$ | 0 | $\frac{1}{2}m'_{44}$ | $\frac{1}{4}m'_{43}$ | $\frac{1}{2}m'_{22} + \frac{1}{4}m'_{33}$ | $\frac{1}{4}m'_{34}$ |
| $48B_n$ | $-m'_{41} - \frac{1}{2}m'_{42}$ | 0 | $-\frac{1}{4}m'_{42}$ | $-\frac{1}{2}m'_{23} + \frac{1}{4}m'_{32}$ | $-\frac{1}{4}m'_{24}$ |

| n | 10 | 11 | 12 |
|---|---|---|---|
| $48A_n$ | $\frac{1}{2}m'_{21} + \frac{1}{4}m'_{22}$ | $-\frac{1}{4}m'_{34}$ | $\frac{1}{4}m'_{22} - \frac{1}{4}m'_{33}$ |
| $48B_n$ | $\frac{1}{2}m'_{31} + \frac{1}{4}m'_{32}$ | $\frac{1}{4}m'_{24}$ | $\frac{1}{4}m'_{23} + \frac{1}{4}m'_{32}$ |

This is done because some of the values are sine values and they have been indicated by A terms and some of them are cosine values in the Fourier series and these are represented by B terms. The numbers from 0 to 12 indicates the number of the term in the Fourier series.

In Table 2, the elements M of the Mueller matrix are shown in terms of the values conducted to it by conductors 48A0–48A12 and 48B1–48B12 with each element of the Mueller matrix being shown with the column of the element indicated by the first digit of the subscript and its row by the second digit of the subscript.

Because the quarter-wave retarders 32 and 38 are synchronized and operate with one being a fixed multiple in frequency of the other in operation of a one to five ratio, the Fourier expression of the signal on conductor 44 is limited to 25 terms which are readily manipulated to calculate the elements of the Mueller matrix. Table 1 expresses the Mueller matrix elements in terms of the coefficients of the Fourier signal analysis with the subscripts referring to the term of the Fourier analysis, A representing a sine term and B a cosine term with the number following the letter indicating the place of the term in the series.

is determined by the effect of the optical system, including the effect of the two modulators on the light. It is further arbitrarily assumed that the part of each element of the Mueller matrix which is caused by the optical system may be considered as a separate matrix that includes constants and variables with the variables being a simple product of the two frequencies of the two modulators.

Secondly, it is believed that the measurement is simplified first by the use of only two modulators because this simplifies the matrix representing the optical system. One modulator provides inadequate information.

Thirdly, it is believed that the measurement is simplified by the synchronization of the two modulators and that this synchronization causes the Mueller matrix that identifies the interaction of the light with the medium to be calculable from the coefficients of a Fourier analysis which has a finite number of terms.

Fourthly, it is still further believed that the process is further simplified because the modulation of one of the two elements is a product or an even multiple of the modulation of the other.

Fifthly, it is believed that a one to five ratio is opti-

TABLE 2

| COLUMN | ROW 1 | ROW 2 | ROW 3 | ROW 4 |
|---|---|---|---|---|
| 1 | $m'_{11} = 48A0 - 48A2 + 48A8 - 48A10 + 48A12$ | $m'_{21} = 2 \times (48A10) - 2 \times (48A8 + 48A12)$ | $m'_{31} = 2 \times (48B10) - 2 \times (48B8 + 48B12)$ | $m'_{41} = 2 \times (48B3) - 48B5$ |
| 2 | $m'_{12} = 2 \times (48A2) - 2 \times (48A8 + 48A12)$ | $m'_{22} = 4 \times (48A8 + 48A12)$ | $m'_{32} = 4 \times (48B8 + 48B12)$ | $m'_{42} = -4 \times (48B3) = -4 \times (48B7) = -2 \times 48B3 + 48B7)$ |
| 3 | $m'_{13} = -2 \times (48B2) - 2 \times (48B12 - 48B8)$ | $m'_{23} = 4 \times (48B12 - 48B8)$ | $m'_{33} = 4 \times (48A8 - 48A12)$ | $m'_{43} = -4 \times (48A3) = 4 \times (48A7) = 2 \times (48A7 - 48A3)$ |
| 4 | $m'_{14} = 48B1 + 2 \times (48B9)$ | $m'_{24} = -4 \times (48B9) = 4(48B11) = 2 \times (48B11 - 48B9)$ | $m'_{34} = 4 \times (48A9) = -4 \times (48A11) - 2 \times (48A9 - 48A11)$ | $m'_{44} = -2 \times (48A4) = 2 \times (48A6) = (48A6 - 48A4)$ |

It is not completely understood why the use of two synchronized quarter-wave retarders on opposite sides of the medium with which the light reacts when modulated in a one to five ratio provides the simple relationships expressed in Tables 1 and 2. However, it is believed that there are a number of separate steps to the process which simplifies the relationship, each of which individually simplifies the amount of work necessary to convert the measurements into a meaningful Mueller matrix that identifies the characteristics of the medium.

Firstly, the understanding that there are a number of parts to the process of simplification is based on the principle of superposition or the concept that each of the elements of the Mueller matrix may be composed of two separate parts, one of which is determined by the effect of the medium on the light and the other of which mum athough this is not known as a provable certainty.

Table 1 results from a substitution into the relationships described above of the frequencies of modulation of one to five. The table occurs in substantially the same form regardless of whether the faster retarder is before the light reaches the medium or after. A better understanding of this relationship can be obtained from the paper by R. M. A. Azzam entitled "Photopolarimetric Measurement of the Mueller Matrix by Fourier Analysis of a Single Detected Signal", published by Optics Letters, Vol. 2, No. 6, June, 1978, pgs. 148–150.

The Fourier signal analyzer 46 may be of any type. For example, Fourier analyzers which: (1) filter the different frequency components; (2) separate the sine and cosine functions for each frequency by phase detection; and (3) gate these functions to the output conductors by the signal from which these synchronizing signal sources are suitable. Also, harmonic coefficient generators of the type disclosed in U.S. Pat. No. 2,752,092 which modulate the total signal by each of the frequencies selectively and perform the known integration to generate the coefficients for each term are suitable. Whichever type of Fourier signal analyzer is used, the coefficients for each term is gated to the appropriate conductors 48A0–48A12 and 48B1–48B12 (four of which are shown in FIG. 1). Many different versions of analog and digital Fourier signal analyzers are available and may be adapted for use with the invention.

Figure 2:
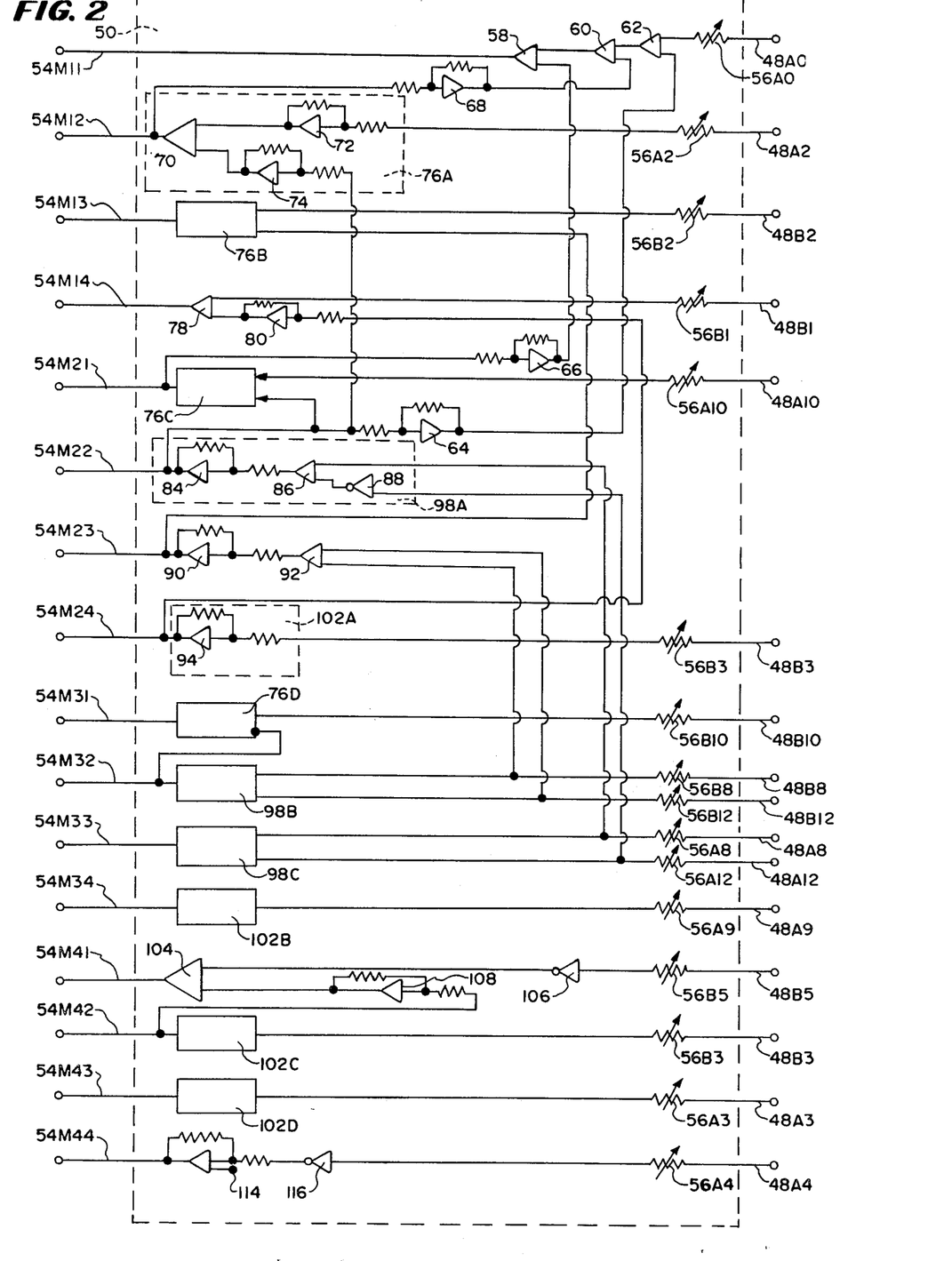
FIG. 2 is a logic circuit diagram of a portion of the embodiment of FIG. 1.

In FIG. 2, there is shown a logic circuit diagram of the Mueller matrix converter 50 having connected to it input conductors 48A0, 48A2, 48B2, 48B1, 48A10, 48B3, 48B10, 48B8, 48B12, 48A8, 48A12, 48A9, 48B5, 48B3, 48A3 and 48B4 having output conductors 54M11–54M44. The output conductors carry the 16 elements of the 4×4 Mueller matrix signals on them and the input conductors are connected to the Fourier signal analyzer 46 to receive the corresponding coefficients of the Fourier analysis from the detector 42 (FIG. 1). The outputs are connected to the recorder or display 52 (FIG. 1) to display the numerical values of the elements of the Mueller matrix to provide information about the sample contained in the sample cell 20. While an analog Mueller matrix converter 50 is shown in FIG. 2, a digital calculator would of course be used if the Fourier signal analyzer 46 were a digital instrument.

The Mueller matrix converter 50 performs the function of calibrating or normalizing the circuitry and of calculating the actual elements of the coefficients of the Fourier analyzer. There are surplus coefficients which are not used but could be used as can be seen from Table 1 since alternate coefficients may be used with slightly different arithmetic functions being performed. Those additional coefficients can be used for error checking or correcting if desired, although that is not shown in FIG. 2.

To provide a signal for column 1, row 1 ($M_{11}$) of the Mueller matrix to the conductor 54M11, the Mueller matrix converter 50 includes three differential operational amplifiers 58, 60 and 62 and three operational amplifiers 64, 66 and 68.

The conductor 48A0 is electrically connected through the potentiometer or variable resistor 58A0 to the positive input terminal of the differential amplifier 62. The inverting input of the differential amplifier 62 is electrically connected to conductor 54M22 through the operational amplifier 64, which has its input and feedback resistors adjusted to multiply its input from conductor 54M22 by one fourth and apply it to amplifier 62.

The output of the differential amplifier 62 is connected to the positive input terminal of the differential amplifier 60 and provides to it the signal from conductor 48A0 minus the signal on conductor 54M22 divided by one fourth. The negative or inverting input of the differential amplifier 60 is electrically connected to conductor 54M12 through the operational amplifier 68 which is adjusted to divide the signal on conductor 54M12 by one half by an adjustment of its feedback and input resistor.

The output of the differential amplifier 60 is connected to the positive input of differential amplifier 58 and applies a signal to that input which is equal to a signal on conductor 48A0 as calibrated by potentiometer 56A0 minus one half of the signal on conductor 54M12 and one fourth of the signal on conductor 54M22. The other input of the differential amplifier 58 is electrically connected to conductor 54M21 through the operational amplifier 66 which is adjusted to divide its input signal by one half.

The output of the differential amplifier 58 is electrically connected to conductor 54M11 to provide to that conductor a signal which is equal to the signal for conductor 48A0 as calibrated by the potentiometer 56A0 minus one half the signal on conductor 54M12, one half of the signal on conductor 54M21 and one fourth of the signal on the conductor 54M22. This output is equal to the element of the Mueller matrix in position 11.

To provide a signal for column 1, row 2 ($M_{12}$) of the Mueller matrix on conductor 54M12, the Mueller matrix converter includes a differential amplifier 70 and two operational amplifiers 72 and 74. The positive or non-inverting input of the differential amplifier 70 is electrically connected to conductor 48A2 through the calibration potentiometer 56A2 and the operational amplifier 72 which is adjusted to multiply the signal by two. The inverting or negative input terminal of the differential amplifier 70 is electrically connected to conductor 54M22 through the operational amplifier 74, which is adjusted to divide the signal by one half. The output of the differential amplifier 70 is electrically connected to conductor 54M12 to provide a signal which is equal to two times the signal on conductor 48A2 as calibrated minus one half the signal on conductor 54M22, this signal being equal to the element in the Mueller matrix at position 12.

To provide a signal on conductor 54M13 equal to the element in the Mueller matrix at column 1 row 3, the output conductor 54M13 is electrically connected to the output of a circuit 76B which is identical to the circuit 76A to which conductor 54M13 is connected. One of the two inputs to that circuit is electrically connected through a potentiometer 56B2 to the conductor 48B2 and the other is electrically connected to conductor 54M23. The input signals to the circuit 76B differ from the input signals to the circuit 76A that includes differential amplifier 70 and operational amplifier 72 and 74 but otherwise the circuits are the same.

To provide the Mueller matrix element $M_{14}$ to conductor 54M14, the Mueller matrix converter 50 includes a differential amplifier 78 and an operational amplifier 80 with one input to the differential amplifier 78 being electrically connected through the calibration potentiometer 56B1 to conductor 48B1 and with the other or negative input to the differential amplifier 78 being electrically connected through the operational amplifier 80 to conductor 54M24. The differential amplifier 80 is adjusted to divide the output on conductor 54M24 in half.

To provide a value equal to the Mueller matrix element $M_{21}$ to conductor 54M21, the Mueller matrix converter 50 includes a circuit 76C identical to the circuit 76A. The output of the circuit 76C is electrically connected to conductor 54M21 and one of its inputs is connected through the calibration potentiometer 56A10 to conductor 48A10 and the other is electrically connected to the output of conductor 54M22.

To provide the Mueller matrix element $M_{22}$ to conductor 54M22, the Mueller matrix converter 50 includes an operational amplifier 84, a differential amplifier 86 and an inverter 88. Conductor 48A12 is electrically connected through the calibrating potentiometer 56A12 to the input of the inverter 88, the output of the inverter 88 being electrically connected to the negative or inverting terminal of the differential amplifier 86. The other input or positive input of the differential amplifier 86 is electrically connected to conductor 48A8 through the calibration potentiometer 56A8 so that the signals on conductors 48A8 and 48A12 are added. The output of the differential amplifier 86 is connected to conductor 54M22 through the operational amplifier 84, with the operational amplifier 84 being adjusted to multiply the input signal by 4.

To provide a potential which is of the value of the Mueller matrix element $M_{23}$ to conductor 54M23, the Mueller matrix converter includes an operational amplifier 90 and a differential amplifier 92. The positive input of the differential amplifier 92 is electrically connected to conductor 48B12 through calibration potentiometer 56B12 and the inverting or negative terminal is electrically connected to 48B8 through calibrating potentiometer 56B8. The output of the differential amplifier 92 is connected to conductor 54M23 through the operational amplifier 90 which is adjusted to multiply by four.

To provide a value of potential which is equal to the Mueller matrix element $M_{24}$ to conductor 54M24, the Mueller matrix converter 50 includes an operational amplifier 94 having its output electrically connected to conductor 54M24 and its input electrically connected to conductor 48B3 through the calibration potentiometer 56B3, the operational amplifier 94 having values of feedback and input resistances which cause it to multiply its input signal by four.

To provide an output signal to conductor 54M31 which is equal in value to Mueller matrix element $M_{31}$, the Mueller matrix converter 50 includes a circuit 76D which is the same as the circuit 76C except that its output is electrically connected to conductor 54M31 rather than 54M21, one of its inputs is electrically connected to conductor 48B10 through the calibration potentiometer 56B10 and its other conductor is electrically connected to conductor 54M32.

To apply a potential to conductor 54M32 which is equal in value to the Muller matrix element $M_{32}$, the Mueller matrix converter 50 includes a circuit 98B which is identical to the circuit 98A connected to conductor 54M22 except that its output is electrically connected to conductor 54M32 rather than to conductor 54M22 and one of its inputs is electrically connected to conductor 48B8 through the calibration potentiometer 56B8 and its other is electrically connected to conductor 48B12 through the calibration potentiometer 56B12.

To provide a potential to conductor 54M33 which is equal in value to the Mueller matrix element $M_{33}$, the Mueller matrix converter 50 includes a circuit 98C which is identical to the circuit 98A except that its output is electrically connected to conductor 54M33, one input is electrically connected to conductor 48A8 through the adjusting potentiometer 56A8 and its other input is electrically connected to conductor 48A12 through the adjusting potentiometer 56A12.

To provide a potential to conductor 54M34 which is equal to the Mueller matrix element $M_{34}$, the Mueller matrix converter 50 includes a circuit 102B which is the same as the circuit 102A that includes the operational amplifier 94 except that its output is electrically connected to conductor 54M34 and its input is electrically connected to conductor 48A9 through a calibration potentiometer 56A9.

To provide a potential to conductor 54M41 which is equal in value to the Mueller matrix element $M_{41}$, the Mueller matrix converter 50 includes a differential amplifier 104, an inverter 106 and an operational amplifier 108. Conductor 48B5 is electrically connected through the calibration potentiometer 56B5 to conductor 48B5 and the inverter 106 to the non-inverting input of the differential amplifier 104 and conductor 54M42 is electrically connected through the operational amplifier 108 to the inverting or negative terminal of the differential amplifier 104. The operational amplifier 108 is adjusted to multiply by one half and the output of the differential amplifier 104 is electrically connected to conductor 54M41.

To provide an output potential to conductor 54M42 which is equal in value to Mueller matrix element $M_{42}$, the Mueller matrix converter 50 includes a circuit 102C which is identical to circuit 102A and has its output electrically connected to conductor 54M42 and its input electrically connected to conductor 48B3 through the calibration potentiometer 56B3.

To provide an output to conductor 54M43 which is equal in value to the Mueller matrix element $M_{43}$, the Mueller matrix converter includes a circuit 102D which is identical to the circuit 102A and has its output electrically connected to conductor 54M43 and its input electrically connected to conductor 48A3 through the calibration potentiometer 56A3.

To provide a potential to conductor 54M44 which is equal in value to the Mueller matrix element $M_{44}$, the matrix converter 50 includes an operational amplifier 114 which is adjusted to multiply by two and has its output electrically connected to conductor 54M44 and its input electrically connected to conductor 48A4 through the calibration potentiometer 56A4 and the inverter 116.

In use, the Mueller matrix converter 50 is calibrated by applying the beam of light 34 through pure air or vacuum in the sample cell 20. With this arrangement, the calibration potentiometers 56A0 are adjusted for calibration. With pure air as the medium the recorder or display 52 should indicate all zero's except for "one's" along the principal diagonal of the Mueller matrix. This cancels out the irregularities in the optical systems and recorder or display.

Figure 3:
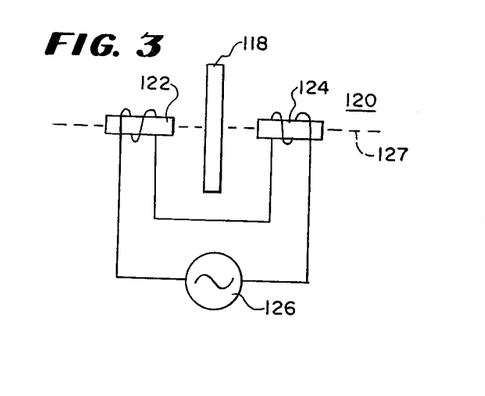
FIG. 3 is a schematic diagram of apparatus for optically rotating an optical element which may be used in an embodiment of FIG. 1.

In FIG. 3, there is shown a novel circuit for rotating an optical element 118. The optical element 118 may be any element through which light passes. However, in the polarimeter of FIG. 1, it is particularly useful for the element 118 to be a mica disc of a quarter-wave retarder such as 32 or 38 (FIG. 1) so that its rotation electronically or optically without actual movement serves to modulate the beams of light 34 and 36 (FIG. 1). However, the embodiment of FIG. 3 has other uses as well.

To rotate the element 118 optically, the optical rotator 120 in FIG. 3 includes first and second Faraday cells 122 and 124 electrically connected to a source of AC signals 126, through windings which are in oppositely disposed relationship so that current biases the Faraday cell 122 in one direction and 124 in the opposite direction by an equal amount during each half cycle of AC signal. Thus, the electromagnetic field applied to the Faraday cell 122 is equal and opposite to the field applied to the Faraday cell 124 so that a beam of light 127 passing through each is rotated in one direction by cell 122 and in the other direction by cell 124. This may be accomplished by applying signals of opposite polarity to the windings or by windings wound oppositely.

The Faraday cells 122 and 124 are on opposite sides of the element 118 and aligned with the beam of light 127 so that the beam of light 127 passes through the first Faraday cell 122 which rotates it in one direction, before it reaches the optical element 118 and, after leaving the optical element 118, it passes through the Faraday cell 124 which rotates it in the opposite direction. The rotation of the light in the two directions is the equivalent optically of rotating the element 118. Consequently, the modulating source 126 modulates the beam of light 127 just as though the quarter-wave retarder 118 was rotated physically.

An explanation of this technique of rotating an object optically by rotating polarized light is given in the article "Simulation of Mechanical Rotation by Optical Rotation: Application to the Design of a New Fourier Photo Polarimeter" by R. M. A. Azzam, J. Opt. Soc. Am., Vol. 68, No. 4, April, 1978, 518–521.

Figure 4:
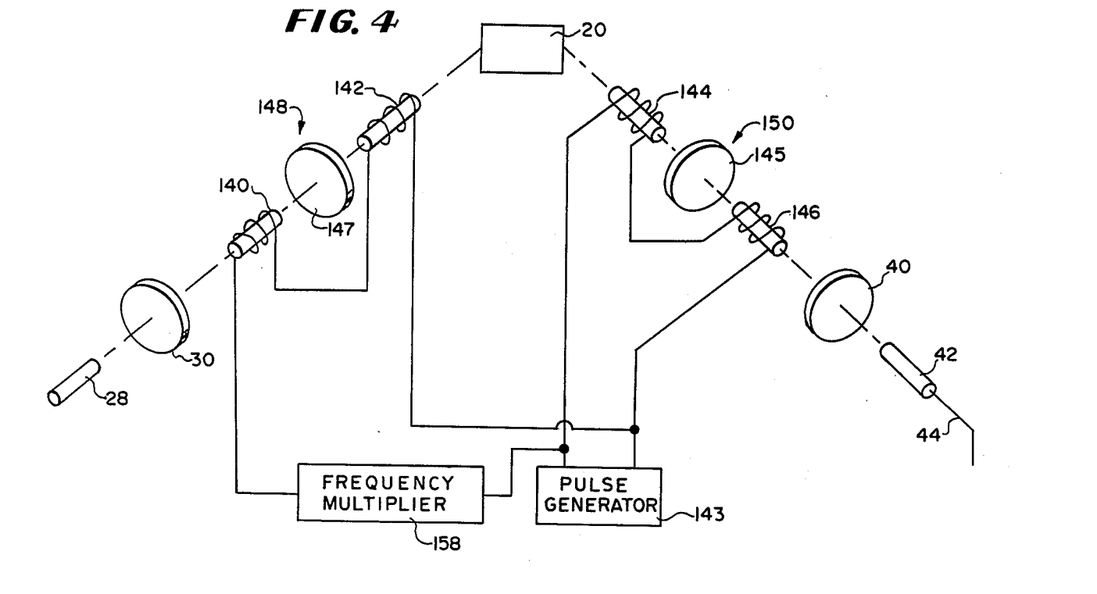
FIG. 4 is a simplified schematic diagram of a polarimeter in accordance with another embodiment of the invention.

In FIG. 4, there is shown a partial schematic diagram of the embodiment of FIG. 1, using the modulator of FIG. 3 rather than the modulator 26. As shown in this view, the identical source of light 28, polarizer 30, sample cell 20, polarizer 40, photodetector 42, and conductor 44 are used to supply a signal to the Fourier signal analyzer 46 (FIG. 1) to develop information for use in a Mueller matrix. However, a different first quarter-wave retarder 148 is used rather than the retarder 32 in the embodiment of FIG. 1 and a different second retarder 150 is used in the embodiment of FIG. 4 rather than the quarter-wave retarder 38 which is used in the embodiment of FIG. 1. The retarders 148 and 150 operate in accordance with the principle described in FIG. 3.

To provide quarter-wave modulation, a pulse generator 123 generates pulses at a selected rate consistent with the condition of the sample cell 20. That is, the frequency of the pulses is set so that if the samples vary in the sample cell 20 such as in a flow cell, the frequency of sampling is fast enough to obtain a readout within 10% of the change.

The pulse generator 143 provides pulses to two Faraday cells 144 and 146 to perform in the manner of the embodiment of FIG. 3 to modulate the light passing through the polaroid sheet 40 to the photocell 42. These pulses are also connected to a frequency multiplier 158 which multiplies the frequency by 5 and applies it to the two Faraday cells 140 and 142 on opposite sides of the disc 147 of the quarter-wave retarder 148.

Because the Faraday cells 144 and 146 are in line with the light passing through a mica disc 145, the quarter-wave retarder 150, and on opposite sides of the disc 145, they rotate the polarized light passing through the retarder. In this way, the retarder 150 includes a mica plate 145 which retards the light by a quarter wave as it passes through at the frequency set by the pulse generator 143. The mica plate 147 or other quarter-wave retarder between the Faraday cells 140 and 142 operates in a similar manner to modulate the light at a frequency one fifth of that modulated by the mica plate 145. As can be understood, the end result is the same as that with the embodiment of FIG. 1 but the mechanical rotation of the half quarter-wave retarders is avoided.

Several examples of the use of the polarimeters of FIGS. 1 and 4 are given below.

EXAMPLE 1

The sample cell 20 is an isotropic surface from which the beam of light 34 (FIG. 1) is reflected to form the beam 36. With this arrangement, the optical system can be represented by the Mueller matrix shown in Table 3.

In Table 3 the tangent of psi represents the differential attenuation of the two basic polarization components which are parallel and perpendicular to the plane of incidence of the light. Delta represents the difference in phase shift experienced by those same polarizations upon reflection. Thus, the symbol psi and delta represent well known characteristics of an isotropic surface, which can be calculated by the Mueller matrix in a known way.

TABLE 3

$$M = \begin{pmatrix} 1 & -\cos2\psi & 0 & 0 \\ -\cos2\psi & 1 & 0 & 0 \\ 0 & 0 & \sin2\chi\cos\Delta & \sin2\chi\sin\Delta \\ 0 & 0 & -\sin2\chi\sin\Delta & \sin2\chi\cos\Delta \end{pmatrix}$$

The zero values shown in the matrix of Table 3 are always zero for light reflected from an isotropic surface. If they are not zero, then their value indicates that the surface is not purely isotropic or that the measuring instrument is not calibrated properly.

EXAMPLE 2

Modulated monochromatic light in the beam 34 (FIG. 1) is transmitted to an optically anisotropic medium with combined birefringence and linear dichroism along the same axes. The Mueller matrix representing the characteristics of the anisotropic medium is given in Table 3 and it is the same for example 1 (Table 3).

The values of delta and tangent of psi are given in Equation 1. In this equation "d" represents the distance traveled through the medium, lambda is the vacuum wave length of light, $K_o$ and $K_e$ are the ordinary and extraordinary extinction coefficients of the medium and $n_o$ and $n_e$ are the ordinary and extraordinary refractive indices of the medium.

EQUATION 1

$$M = \text{same as in 1 where } \tan\psi = \exp\left[-\frac{2d\pi}{\lambda}(k_e - k_o)\right]$$

$$\Delta = -\frac{2\pi d}{\lambda}(n_e - n_o)$$

Fourier terms corresponding to the lines of 48 for Table 3 are given in Table 4.

EXAMPLE 3

The light beam 34 is modulated and transmitted through an optically anisotropic medium with arbitrary orthogonal elliptical eigenpolarizations. The Mueller matrix representing the optical system is given in Table 5 for this example. In this table, omega represents the elliptical birefringence of the medium; tau represents the distance through the medium; and mu, nu and eta are elements of the normalized orthogonal Stokes eigenvectors. The terms in the Fourier analysis are given in Table 6.

EXAMPLE 4

The light beam 34 is transmitted through a medium in 20 which includes a system of spherical optically isotropic particles. The terms of the Fourier analysis are given in Table 7 and the Mueller matrix in Table 8.

TABLE 4

| n | 0 | 1 | 2 | 3 | 4 | 5 | 6 |
|---|---|---|---|---|---|---|---|
| $48A_n$ | $5/4 - \cos2\psi$ | 0 | $-\frac{1}{2}\cos2\psi + \frac{1}{4}$ | $-\frac{1}{4}\sin2\psi\sin\Delta$ | $-\frac{1}{4}\sin2\psi\cos\Delta$ | 0 | $\frac{1}{8}\sin2\psi\cos\Delta$ |
| $48B_n$ | 0 | 0 | 0 | 0 | 0 | 0 | 0 |

| n | 7 | 8 | 9 | 10 | 11 | 12 |
|---|---|---|---|---|---|---|
| $48A_n$ | $-\frac{1}{4}\sin2\psi\sin\Delta$ | $\frac{1}{8}(1 + \sin2\psi\cos\Delta)$ | $\frac{1}{4}(\sin2\psi\sin\Delta)$ | $-\frac{1}{2}\cos2\psi + \frac{1}{4}$ | $-\frac{1}{4}(\sin2\psi\sin\Delta)$ | $\frac{1}{8}(1 - \sin2\psi\cos\Delta)$ |
| $48B_n$ | 0 | 0 | 0 | 0 | 0 | 0 |

TABLE 5

$$M = \begin{pmatrix} 1 & 0 & 0 & 0 \\ 0 & \cos\omega\tau + \eta^2(1 - \cos\omega\tau) & \mu\sin\omega\tau - \nu\eta(1 - \cos\omega\tau) & \nu\sin\omega\tau + \mu\eta(1 - \cos\omega\tau) \\ 0 & -\mu\sin\omega\tau - \nu\eta(1 - \cos\omega\tau) & \cos\omega\tau + \nu^2(1 - \cos\omega\tau) & \eta\sin\omega\tau - \mu\nu(1 - \cos\omega\tau) \\ 0 & -\nu\sin\omega\tau + \mu\eta(1 - \cos\omega\tau) & -\sin\omega\tau - \mu\nu(1 - \cos\omega\tau) & \cos\omega\tau + \mu^2(1 - \cos\omega\tau) \end{pmatrix}$$

TABLE 6

| n | 0 | 1 | 2 | 3 |
|---|---|---|---|---|
| $48A_n$ | $\frac{1}{4}[1 + (\cos\omega\tau + \eta^2(1 - \cos\omega\tau))]$ | 0 | $\frac{1}{4}(\cos\omega\tau + \eta^2(1 - \cos\omega\tau))$ | $-\frac{1}{4}(-\eta\sin\omega\tau - \mu\nu(1 - \cos\omega\tau))$ |
| $48B_n$ | 0 | $\frac{1}{2}(\nu\sin\omega\tau + \mu\eta(1 - \cos\omega\tau))$ | $\frac{1}{4}(\mu\sin\omega\tau - \nu\eta(1 - \cos\omega\tau))$ | $-\frac{1}{4}(-\nu\sin\omega\tau + \mu\eta(1 - \cos\omega\tau))$ |

| n | 4 | 5 | 6 | 7 |
|---|---|---|---|---|
| $48A_n$ | $-\frac{1}{4}(\cos\omega\tau + \mu^2(1 - \cos\omega\tau))$ | 0 | $\frac{1}{4}(\cos\omega\tau + \mu^2(1 - \cos\omega\tau))$ | $\frac{1}{4}(-\eta\sin\omega\tau - \mu\nu(1 - \cos\omega\tau))$ |
| $48B_n$ | 0 | $-\frac{1}{2}(-\sin\omega\tau + \mu\eta(1 - \cos\omega\tau))$ | 0 | $-\frac{1}{4}(-\nu\sin\omega\tau + \mu\eta(1 - \cos\omega\tau))$ |

| n | 8 | 9 | 10 |
|---|---|---|---|
| $48A_n$ | $\frac{1}{4}(\cos\omega\tau + \frac{1}{2}(\eta^2 + \nu^2)(1 - \cos\omega\tau))$ | $\frac{1}{4}(\eta\sin\omega\tau - \mu\nu(1 - \cos\omega\tau))$ | $\frac{1}{4}\cos\omega\tau + \eta^2(1 - \cos\omega\tau))$ |
| $48B_n$ | $-\frac{1}{2}(\sin\omega\tau)$ | $-\frac{1}{4}(\nu\sin\omega\tau + \mu\eta(1 - \cos\omega\tau))$ | $\frac{1}{4}(-\mu\sin\omega\tau - \nu\eta(1 - \cos\omega\tau))$ |

| n | 11 | 12 |
|---|---|---|
| $48A_n$ | $-\frac{1}{4}(\mu\sin\omega\tau - \mu\nu(1 - \cos\omega\tau))$ | $\frac{1}{8}(\eta^2 - \nu^2)(1 - \cos\omega\tau)$ |
| $48B_n$ | $\frac{1}{4}(\nu\sin\omega\tau + \mu\eta(1 - \cos\omega\tau))$ | $-\frac{1}{4}\nu\eta(1 - \cos\omega\tau)$ |

TABLE 7

| n | 0 | 1 | 2 | 3 | 4 | 5 | 6 |
|---|---|---|---|---|---|---|---|
| $a_n$ | $5/4 M_{11} + M_{12}$ | 0 | $\frac{1}{2}M_{12} + \frac{1}{4}M_{11}$ | $+\frac{1}{4}M_{34}$ | $-\frac{1}{4}M_{33}$ | 0 | $\frac{1}{8}M_{33}$ |
| $b_n$ | | 0 | 0 | 0 | 0 | 0 | 0 |

| n | 7 | 8 | 9 | 10 | 11 | 12 |
|---|---|---|---|---|---|---|
| $a_n$ | $-\frac{1}{4}M_{34}$ | $\frac{1}{8}(M_{11} + M_{33})$ | $\frac{1}{4}M_{34}$ | $\frac{1}{2}M_{12} + \frac{1}{4}M_{11}$ | $-\frac{1}{4}M_{34}$ | $\frac{1}{8}(M_{11} - M_{33})$ |
| $b_n$ | 0 | 0 | 0 | 0 | 0 | 0 |

TABLE 8

$$M = \begin{pmatrix} M_{11} & M_{12} & 0 & 0 \\ M_{12} & M_{11} & 0 & 0 \\ 0 & 0 & M_{33} & M_{34} \\ 0 & 0 & -M_{34} & M_{33} \end{pmatrix}$$

EXAMPLE 5

The light beam 34 is transmitted through a randomly oriented collection of particles, each of which may be optically active. The terms in the Fourier analysis are shown in Table 9 and the Mueller matrix in Table 10.

Figure 5:
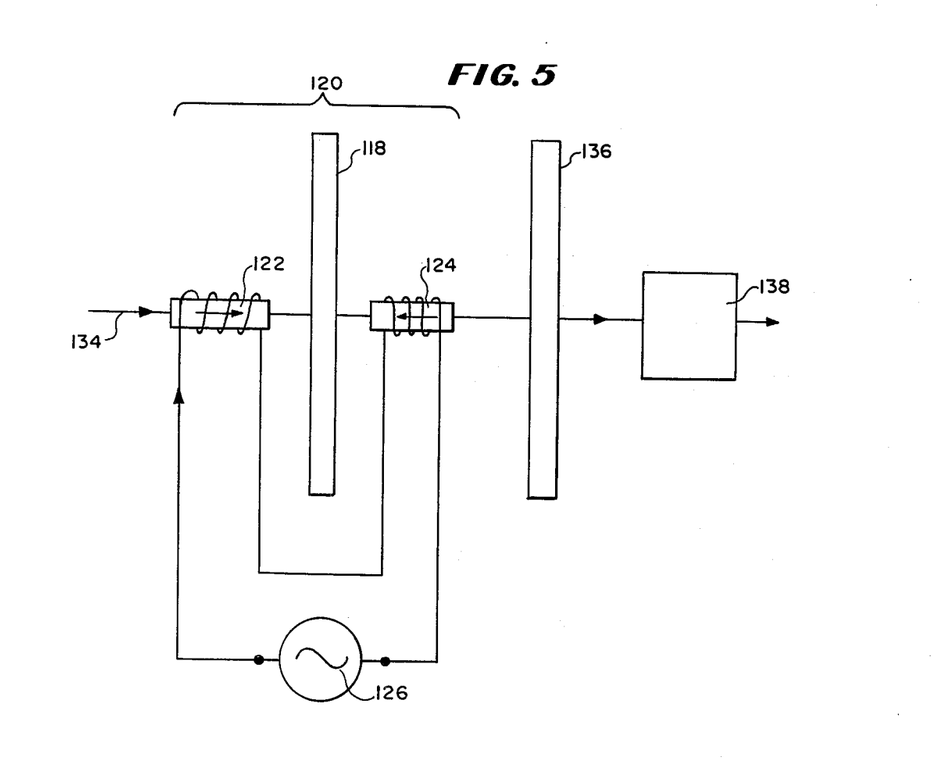
FIG. 5 is an embodiment of another type of polarimeter.

In FIG. 5, there is shown a Fourier photopolarimeter for measuring the state of polarization of light using the optical rotator of FIG. 3. This photopolarimeter may be used as an elipsometer in a known way in the art by analyzing the electrical signal generated by a photoconductor and for this purpose includes: (1) a source of polarized light 134; (2) the optical rotator 120 described in connection with FIG. 3; and (3) a linear polarizer 136 which serves as an analyzing polarizer and a photodetector 138.

This arrangement works substantially in the same manner as the unit of FIG. 3 with the source of potential 126 applying current to windings on the Faraday cells 122 and 124 to rotate the light passing through the quarter-wave retarder 118 in opposite directions to modulate the light before it is passed to the analyzer 136.

TABLE 9

| n | 0 | 1 | 2 | 3 | 4 | 5 | 6 |
|---|---|---|---|---|---|---|---|
| $a_n$ | $M_{11} + M_{12} + \frac{1}{4}M_{22}$ | 0 | $\frac{1}{2}M_{12} + \frac{1}{4}M_{22}$ | $-\frac{1}{4}M_{34} - \frac{1}{4}M_{44}$ | | 0 | $\frac{1}{8}M_{44}$ |
| $b_n$ | 0 | $M_{14} + \frac{1}{2}M_{24}$ | $\frac{1}{2}M_{13} + \frac{1}{4}M_{23}$ | $-\frac{1}{4}M_{24}$ | 0 | $-M_{14} - \frac{1}{2}M_{24}$ | 0 |

| n | 7 | 8 | 9 | 10 | 11 | 12 |
|---|---|---|---|---|---|---|
| $a_n$ | $-\frac{1}{4}M_{34}$ | $\frac{1}{8}(M_{22} + M_{33})$ | $\frac{1}{4}M_{34}$ | $\frac{1}{2}M_{12} + \frac{1}{4}M_{22}$ | $-\frac{1}{4}M_{34}$ | $\frac{1}{8}(M_{22} - M_{33})$ |
| $b_n$ | $-\frac{1}{4}M_{24}$ | $-\frac{1}{4}M_{23}$ | $-\frac{1}{4}M_{24}$ | $-\frac{1}{2}M_{13} - \frac{1}{4}M_{23}$ | $\frac{1}{4}M_{24}$ | 0 |

TABLE 10

| | | | | |
|---|---|---|---|---|
| | $M_{11}$ | $M_{12}$ | $M_{13}$ | $M_{14}$ |
| $M =$ | $M_{12}$ | $M_{22}$ | $M_{23}$ | $M_{24}$ |
| | $-M_{13}$ | $-M_{23}$ | $M_{33}$ | $M_{34}$ |
| | $M_{14}$ | $M_{24}$ | $-M_{34}$ | $M_{44}$ |

The results of this analyzer may be used for elipsometric measurements as known in the art and as more specifically described in the aforementioned publication of R.M.A. Azzam, J. Opt. Soc. Am., Vol. 68, No. 4, April, 1978, 518–521.

As can be understood from the above description, this polarimeter has the advantages of being usable for a number of different applications, resulting in a relatively simple calculation to determine the characteristics of a medium through which light is transmitted and being inexpensive. It is only required to have two moving parts or electrical units which simulate the moving parts to provide modulation of the light transmitted to the medium and from the medium.

The instrument is capable of measuring simultaneously and automatically all 16 elements of the Mueller matrix that characterizes the most general elastic interaction of light with any sample. Consequently, it can be used for studies such as: (1) measuring the density and particle-size distribution of colloidal suspensions and aerosols; (2) meteorological investigations of fog, haze, clouds and rain; and (3) astronomical observations of planetary atmospheres and interplanetary dust.

Moreover, this instrument operates as an ellipsometer for the characterization of surfaces and thin films. In this special application it has several additional advantages, which are: (1) it can readily characterize surface optical anisotropy; and (2) it is essentially self-calibrating.

The instrument measures natural or electrically magnetically induced linear birefringence and linear dichroism as well as circular birefringence (optical rotation) and circular dichroism. These two uses are significant in physics, chemistry, biochemistry and biophysics.

The optical rotator of FIG. 3 has several independent advantages. These stem from its ability to rapidly modulate radiation without being subject to inertial effects.

Although a preferred embodiment has been described with some particularity, many modifications and variations are possible in the preferred embodiment without deviating from the invention. Therefore, it is to be understood that, within the scope of the appended claims, the invention may be practiced other than as specifically described.

What is claimed is:

1. A method of measuring characteristics of a medium from its interaction with light comprising the steps of:
   modulating a beam of light at a first frequency;
   transmitting said beam of light to said medium after modulating it;
   modulating the light leaving said medium at a second frequency;
   one of said steps of modulating the beam of light at a first frequency and modulating the beam of light leaving said medium includes the step of modulating one of the first and second beams to be five times the frequency of the other;
   developing an electrical signal representing the intensity of said light leaving said medium;
   performing Fourier analysis on said electrical signal to develop electrical signals representing the coefficients of the Fourier analysis of said signal; and
   converting said amplitudes to the elements of a Mueller matrix.

2. The method of claim 1 further including the step of displaying said elements of said Mueller matrix.

3. The method of claim 2 in which the step of modulating the first beam of light at a predetermined frequency includes the step of modulating a monochromatic beam of light at said predetermined frequency.

4. A method according to claim 3 in which the step of modulating includes the step of modulating said beam with a quarter-wave retarder.

5. A method according to claim 4 in which the step of modulating a beam of light includes the step of polarizing said first beam of light.

6. A method according to claim 5 in which the term of the Mueller matrix in the second row and fourth column is a measure of a negative four times the amplitude of the ninth sine term in the Fourier series, four times the eleventh sine term in the Fourier series and twice the difference between the eleventh sine term and the ninth sine term.

7. A method according to claim 6 in which the Mueller matrix element in the third row and fourth column is taken to be four times the ninth cosine term in the Fourier series, a negative four times the eleventh cosine term in the Fourier series and twice the difference between the ninth cosine term and the eleventh cosine term of the Fourier series.

8. The method of claim 7 in which the step of determining the Mueller elements includes the step of determining the fourth element in the fourth row of the Mueller matrix by measuring one of a negative two times the fourth cosine coefficient, two times the sixth cosine coefficient and the difference between the sixth cosine coefficient and the fourth cosine coefficient of the Fourier series.

9. A method according to claim 8 in which the step of determining the elements of the Mueller matrix includes the step of determining the element in the fourth row in the third column of the Mueller matrix by measuring one of a negative four times the third cosine term, four times the seventh cosine term, and two times the difference between the seventh cosine term and the third cosine term of the Fourier analysis.

10. A method according to claim 9 in which the step of determining the elements of the Mueller matrix includes the step of determining the element in the fourth row and second column of the Mueller matrix by measuring one of a negative four times the third sine signal of the Fourier analysis, a negative four times the seventh sine term of the Fourier signal and a negative two times the sum of the third sine term and the seventh sine term of the Fourier signal.

11. A method according to claim 1 in which the step of modulating a beam of light at a first predetermined frequency includes the steps of:
   rotating polarized light through a first angle as it approaches a light retarder; and
   rotating light through an equal angle in the opposite direction after the light has passed through said retarder.

12. A method according to claim 1 in which the step of modulating the light leaving said medium includes the steps of:

rotating polarized light through an angle as it approaches a light retarder; and rotating the light through an equal angle in the opposite direction after it leaves said retarder.

13. A polarimeter comprising:

means for applying polarized light modulated at a first frequency to a medium;

means for receiving the modulated light from the medium and modulating it at a second frequency;

one of said first and second frequencies being five times the other;

means for receiving the second modulated light from said means and converting it to an electrical signal;

means for performing Fourier analysis on said electrical signal to develop a plurality of terms of a Fourier analysis representative of said electrical signal;

means for calculating from said terms of said Fourier analysis the elements of a Mueller matrix; and means for indicating the terms of the Mueller matrix.

14. Apparatus according to claim 13 in which said first and second means for modulating are quarter-wave retarders.

15. Apparatus according to claim 14 in which said means for calculating elements of the Mueller matrix includes calibration means for adjusting the Mueller matrix readout to indicate no change when said light is transmitted through a medium having no elastic interaction therewith.

16. Apparatus according to claim 15 in which said means for calculating the elements of said Mueller matrix include a means for measuring one of the negative four times the ninth sine term of the Fourier series, four times the eleventh term of the sine signal or twice the difference between the eleventh sine term and the ninth sine term of the Fourier signal and said display means includes a means for displaying said measured signal.

17. Apparatus according to claim 13 in which said means for applying polarized light includes:

first means for receiving light and rotating it through a predetermined angle;

a retarder positioned to receive said light rotated through said predetermined angle; and second means positioned on the opposite side of said means for receiving light rotating at said predetermined angle for receiving light passing through said retarder and rotating it through said predetermined angle in the opposite direction, whereby said retarder is optically rotated.

18. Apparatus according to claim 13 in which said means for receiving the modulated light from the medium and modulating it at a second frequency includes:

means for rotating said light through a predetermined angle;

a light retarder adapted to receive light from said means for rotating said light through said predetermined angle; and second means for rotating said light through said predetermined angle.

19. A method according to claim 1 in which:

the step of modulating a beam of light at a first frequency includes the step of changing a predetermined characteristic of the beam of light at said first frequency; and the step of modulating the light leaving said medium at a second frequency includes the step of changing said predetermined characteristic of said light at said second frequency.

20. A method according to claim 19 in which:

the step of modulating a beam of light at a first frequency includes the step of altering a predetermined optical characteristic of a first optical element positioned within said beam of light at said first frequency, whereby said beam of light has an optical characteristic modulated at said first frequency; and the step of modulating the light leaving said medium at a second frequency includes the step of altering said predetermined optical characteristic of a second optical element substantially the same as said first optical element positioned within said beam of light at said second frequency, whereby said predetermined characteristic of the light is modulated at said second frequency.

21. A method according to claim 20 in which:

said step of modulating a beam of light at a first frequency includes the step of moving a first light-wave retarder in said beam of light at said first frequency; and the step of modulating the light leaving said medium at a second frequency includes the steps of moving a second light-wave retarder in said beam of light at said second frequency.

22. A method according to claim 21 in which:

the step of modulating a beam of light at a first frequency includes the step of rotating said first light-wave retarder within said beam of light at a first frequency; and the step of modulating the light leaving said medium at a second frequency includes the step of rotating said second light-wave retarder at said second frequency in said beam of light.

23. A method according to claim 20 in which:

the step of modulating a beam of light at a first frequency the step of simulating the rotation of a first light-wave retarder in said beam of light at a first frequency;

the step of simulating the rotation of said first light-wave retarder including the step of optically rotating light in a first direction through an angle that increases with time at a predetermined rate on one side of said first light-wave retarder, transmitting said light from said light beam after it has been rotated through said light-wave retarder and rotating said light in a second direction at the predetermined rate, whereby said light-wave retarder is optically rotated while remaining stationary;

the step of modulating the light leaving said medium at a second frequency includes the step of simulating rotation of a light-wave retarder in said beam of light;

the step of simulating the rotation of a light-wave retarder including the steps of rotating said beam of light in a first direction through an angle which increases with time at a second predetermined rate; transmitting said light after it has been rotated through said second light-wave retarder and rotating said light in a second direction after it passes through said light-wave retarder at said second predetermined rate, whereby said second light-wave retarder is optically rotated while remaining physically stationary.

24. A polarimeter according to claim 13 in which:

said means for applying polarized light modulated at a first frequency to a medium includes means for transmitting a beam of light to said medium and first modulating means positioned in said beam of light for changing a predetermined characteristic of said light at a first frequency; and said means for receiving the modulated light from the medium and modulating it at a second frequency includes second modulating means positioned in said modulating light from said medium for changing said predetermined characteristic at said second frequency.

25. A polarimeter according to claim 24 in which:

said first modulating means includes a first optical element capable of changing said characteristic of light and a means for moving said first optical element at said first frequency; and said second modulating means includes a second optical element for changing said predetermined characteristic and a means for moving said second optical element at said second frequency.

26. A polarimeter in accordance with claim 25 in which said first and second optical elements are light-wave retarders.

27. A polarimeter according to claim 26 in which:

said means for moving said first optical element is a means for rotating a first of said light-wave retarders; and said means for moving said second optical element is a means for rotating said second of said light-wave retarders.

28. A polarimeter according to claim 27 in which:

said first light-wave retarder is a quarter-wave retarder;

said means for rotating a first of said light-wave retarders is a means for rotating said first quarter-wave retarder about an axis centered in said beam of light at a first frequency;

said second light-wave retarder is a second quarter-wave retarder; and said means for rotating a second of said light-wave retarders includes a means for rotating said second quarter-wave retarder about an axis centered in said beam of light at said second frequency.

29. A polarimeter according to claim 24 in which:

said first modulating means includes a first light-wave retarder positioned within said beam of light; first means for rotating light in said beam of light before it reaches said first light-wave retarder through an angle that increases with time at a predetermined rate in a first direction and means for rotating said light in a second direction opposite to said first direction after it passes through said first light-wave retarder at said predetermined rate, whereby said first light-wave retarder is optically rotated while remaining physically stationary;

said second modulating means including a second light-wave retarder positioned in said beam of light; first means for rotating said light in a first direction through an angle that increases with time at a second predetermined rate and second means for rotating said light in a second direction opposite to said first direction after it has passed through said second light-wave retarder at said second predetermined rate, whereby said second light-wave retarder is optically rotated at said second rate while remaining physically stationary.

* * * * *

UNITED STATES PATENT AND TRADEMARK OFFICE
CERTIFICATE OF CORRECTION

PATENT NO. : 4,306,809
DATED : December 22, 1981
INVENTOR(S) : R.M.A. Azzam

It is certified that error appears in the above—identified patent and that said Letters Patent is hereby corrected as shown below:

Column 7, line 17, change "48B4" to --48A4--;

Column 9, line 40, change "Muller" to --Mueller--;

Column 10, line 39, change "zero's" to --zeros--;

Column 10, line 39, change "one's" to --ones--;

Table 3, row 3, column 3, change "sin2χcosΔ" to
    --sin2ψcosΔ--;

Table 3, row 3, column 4, change "sin2χsinΔ" to
    --sin2ψsinΔ--;

Table 3, row 4, column 3, change "-sin2χsinΔ" to
    -- -sin2ψsinΔ--;

UNITED STATES PATENT AND TRADEMARK OFFICE
CERTIFICATE OF CORRECTION

PATENT NO. : 4,306,809
DATED : December 22, 1981
INVENTOR(S) : R.M.A. Azzam

It is certified that error appears in the above—identified patent and that said Letters Patent is hereby corrected as shown below:

Table 3, row 4, column 4, change "$\sin 2\chi \cos\Delta$" to -- $\sin 2\psi \cos\Delta$ --;

Table 5, row 3, change "$-\sin\omega\tau - \mu\nu(1-\cos\omega\tau)$" to -- $-\eta\sin\omega\tau - \mu\nu(1-\cos\omega\tau)$ --;

Table 6, row 4, change "$-\frac{1}{2}(-\sin\omega\tau + \mu\eta(1-\cos\omega\tau))$" to -- $-\frac{1}{2}(-\nu\sin\omega\tau + \mu\eta(1-\cos\omega\tau))$ --;

Table 6, row 5, change "$\frac{1}{2}\cos\omega\tau + n^2(1-\cos\omega\tau))$" to -- $\frac{1}{2}(\cos\omega\tau + n^2(1-\cos\omega\tau))$ --.

IN THE CLAIMS:

Column 18, line 36, after "frequency" add --includes--.

Signed and Sealed this

First Day of June 1982

[SEAL]

Attest:

GERALD J. MOSSINGHOFF

Attesting Officer      Commissioner of Patents and Trademarks